US005674532A

United States Patent [19]
Atzl et al.

[11] Patent Number: 5,674,532
[45] Date of Patent: Oct. 7, 1997

[54] PANCREATIN PREPARATIONS

[75] Inventors: Günther Atzl, Kufstein; Franz Langer, Mödling; Herbert Polleres, Kufstein, all of Austria

[73] Assignee: Biochemie Gesellschaft m.b.H., Kundl, Austria

[21] Appl. No.: 466,303

[22] Filed: Jun. 6, 1995

Related U.S. Application Data

[63] Continuation of Ser. No. 243,667, May 16, 1994, abandoned, which is a continuation of Ser. No. 720,807, filed as PCT/EP90/02016 Nov. 26, 1990, abandoned.

[30] Foreign Application Priority Data

Nov. 24, 1989 [AT] Austria .................. A2688/89

[51] Int. Cl.$^6$ ................................................ A61K 9/14
[52] U.S. Cl. .................... 424/489; 424/490; 514/951
[58] Field of Search .......................... 424/489, 494, 424/497, 451, 452, 464, 465, 490, 458

[56] References Cited

U.S. PATENT DOCUMENTS

| | | | |
|---|---|---|---|
| 4,019,958 | 4/1977 | Hell et al. | 195/62 |
| 4,623,624 | 11/1986 | Schultze | 435/186 |
| 4,797,287 | 1/1989 | Pich et al. | 424/464 |

*Primary Examiner*—Thurman K. Page
*Assistant Examiner*—James M. Spear
*Attorney, Agent, or Firm*—John L. Chiatalas; Melvyn M. Kassenoff

[57] ABSTRACT

A process for the production of a dry pancreatin preparation is characterized in that the still moist pancreatin mass, which is obtained after extraction with a solvent or solvent mixture, is treated, before the solvents are finally removed, for a short time in a vacuum cutter, until the mass has been divided and shaped into small spherical particles, and then is finally dried.

9 Claims, No Drawings

PANCREATIN PREPARATIONS

This is a continuation of application Ser. No. 08/243,667, filed May 16, 1994, which in turn is a continuation of application Ser. No. 07/720,807, filed Jul. 23, 1991, now both abandoned, which is a 371 of PCT/EP90/02016, filed Nov. 26, 1990.

This invention relates to pancreatin preparations. These are employed in human and veterinary medicine in various presentations. They serve to eliminate or improve enzyme deficiencies, often caused by pathological changes to the pancreas, which may seriously affect the digestive processes. The active substance used in such preparations is particularly pancreatin, which is obtained from the pancreas of pigs. Pancreases removed after slaughter are deep-frozen as quickly as possible, collected together, crushed, treated with additives to stabilize enzymes, if necessary undergo maturing processes, and are finally defatted and dehydrated. If desired, inactive fibrous tissue can also be removed from the glands during the course of processing, and thus an enzyme-rich pancreatin concentrate may be produced. Basically, either dehydration (e.g. lyophilisation) may take place carefully and defatting may follow using an organic solvent, or the fat and water can be removed together using a solvent or a solvent mixture. In all cases, an unshaped product which is moist with solvent, hereinafter called pancreatin pulp, is obtained, and this must then be dried carefully. Size reduction then follows (e.g. grinding) and/or shaping in a dry (e.g. compacting) or wet state (e.g. extruding, granulating, pelletting), in subsequent steps which finally lead to a pancreatin product of the desired quality, from which a particular form for administration may be prepared.

Desired pancreatin qualities accordingly include the capability to form a powder or granulate (e.g. compactate). Desired finished forms for administration include gastric-juice-resistant tablets, dragees or capsules, as well as gastric-juice-resistant particles. Such end products and processes for their production are described for example in EP 0184754, EP 0021129 or DOS 2626109.

Preferably, the finished forms for administration should satisfy the following criteria:
high enzyme content
resistance to gastric juices
capability to disperse as widely as possible over the whole stomach
rapid release of enzyme activity in the small intestine, and
inexpensive method of preparation carried out under mild conditions.

This ideal cannot easily be realised, since the number of required processing steps previously used not only gives rise to considerable costs, but also often leads to a substantial enzyme loss. In addition, contact with the easily dust-forming pancreatin requires protective measures for personnel to counteract the aggressive effect of the product on the skin and mucous membrane, and to avoid allergies. Addition of binding and lubricating agents in the final product is sometimes necessary.

We have now found that a pancreatin mass, e.g. pancreatic pulp, which is already defatted and dehydrated, but is still moist with solvent, such as that remaining in lump-form or paste-form following the extraction with organic solvents, or wetted pancreatin concentrate or powder may be surprisingly converted directly to a very acceptable galenic form.

In a first aspect the present invention provides a process for the production of pancreatin spherical particles which comprises (i) rotating a pancreatin mass moist with solvent around a first axis, and (ii) simultaneously reducing the size of the mass by knives rotating around a second axis, whilst some of the solvent is removed, the first and second axes being at an angle to one another, and either (a) the axes are perpendicular or substantially perpendicular to each other or (b) the arrangement is such that the mass undergoes a rolling motion.

Preferably the two axes are perpendicular or substantially perpendicular to each other. Preferably the first axis is vertical or substantially vertical. Conveniently the second axis is horizontal or substantially horizontal.

In a preferred embodiment the pancreatic mass is rotated horizontally around the hives. Preferably the distance between the two axes is at least the radius of the knives.

In accordance with the invention the pancreatin mass undergoes short treatment in a so-called "cutter" prior to the final drying. Cutters are devices which are used in the foodstuff industry to reduce in size pieces of meat to a pulp. These machines may have of a set of rapidly rotating knives, which set is in a similarly rotating vessel (or tray) containing the pulp to be cut. Thus, the substances in the vessel are repeatedly exposed for short periods to the cutting action of the knives. The degree of the size reduction can be controlled very exactly by choosing the duration of rotation of the knives and vessel. With conventional cutters, the axes of rotation of the vessel and knives are identical or parallel. In accordance with the invention, preferably a cutter is used, in which the axis of rotation of the vessel and the axis of rotation of the stirring arm with knives are perpendicular (or substantially so) to each other.

In the process of the invention because of the angle of the axes, not only a size reduction takes place, but also a rolling motion may take place which generates the spherical particles.

A preferred cutter used in accordance to the invention may comprise a rotating vessel to carry the pancreatin mass. A perpendicular arm has removable curved knives, e.g. 3 to 6 knives. The distance between the rotation axis of the vessel and the axis of the knives may be at least the radius of the rotating knives. With this arrangement of the two axes, there is not only the expected effect of size reduction, but at the same time a rolling effect is provided which results in spherical particles, the size and surface constitution of which are controllable.

The cutter is preferably made out of stainless steel. The cutter has for example a content of 10 to 500 liters, preferably about 50 to 150 liters. The rotational speed of the vessel and the rotating knives may be adjustable in a typical machine. Thus there may be a multi-stage speed adjustment, for example 2 or 3 steps. The rotational speed of the vessel may be from e.g. 9 to 18 rpm, and the rotational speed of the rotating knives is from e.g. 400 to 3000 rpm.

The cutter is for example mounted in a vacuum chamber. For the process of the invention, e.g. as described in the Examples hereinafter, a vacuum of about 1000 to 100 mbar is preferably applied. After the process is finished, the vacuum is preferably removed in order to aerate and homogenize the product.

Cutters of this type are for example described e.g. by H. A. Leniger and W. A. Beverloo "Food process engineering", D. Reidel Publishing Company, Dordrecht, Holland, 1975, at page 185.

When a pancreatin mass which is still moist with a solvent (e.g. moist with acetone containing water) undergoes treatment in such a cutter, even after a short (3–30 minutes) treatment time for breaking up the mass, the formation of spherical particles (pellets) may be surprisingly observed. Any appropriate solvent may be used, but most preferably at least some water is present, e.g. amounts from 5 to 20% by volume. The diameter thereof gradually decreases in time and can be stopped at a desired size. Upon continued size reduction, the spherical particles formed may be further reduced in size, and the result may be a powdery, partly fibrous material. This, after a short treatment time, may be restored to a larger sized particle form by adding an organic solvent, preferably acetone, or the material can be further processed as a powdery product.

During treatment in the cutter, much of the solvent contained therein may be simultaneously evaporated due to the energy employed, with the result that the spherical particles formed are obtained in substantially dry and solid form. The use of a vacuum cutter facilitates control of this part of the process.

The particles obtained by the above-described process may be subsequently completely dried in a conventional device e.g. a conical vacuum drier or a fluidised bed drier without materially changing its shape. Dust-forming material may be removed by a sieve, and if necessary classification according to particle size may be undertaken.

For subsequent galenic use, the particles thus obtained have a very favourable bulk density, and good pourability.

Depending on the desired usage, soft particles with low bulk density may be produced, or if desired hard, mechanically more stable particles with a higher bulk density may be produced.

In a further embodiment of the invention pancreatin concentrates which are moist with a solvent, such as are obtained by carrying out a fibre separation step as described above, are treated by the process of the invention in a vacuum cutter, into similarly spherical, mechanically stable particles.

The inventive process requires a procedure of only a few minutes additional to the normal technical process of drying pancreatin or pancreatin concentrates, yet renders unnecessary any subsequent, complicated, often high-loss shaping operation for galenic formulation, which operation is also unpleasant for the operating personnel.

For filling into capsules, the particles should have the highest bulk density possible, so that the highest enzyme dose possible may be administered in the capsule. In an embodiment of the process according to the invention, particles with a bulk density (i.e. density of freshly shaken material) of more than 0.6 g/ml e.g. up to 0.9 g/ml may be obtained by adding water prior to size reduction, and then drying, e.g. in a conical vacuum drier.

Furthermore, already dry particles with a low bulk density, which have been prepared by the process according to the invention, may be converted by the process according to the invention into a dry granulate with a high bulk density by treating with water or with mixtures of water and organic solvents—preferably acetone.

Similarly particles with a high bulk density may be produced from an already dry pancreatin powder, by wetting with organic solvents—preferably acetone—and water, in a (vacuum) cutter and (vacuum) drier.

Particles thus prepared show only slight reduction in enzymatic activity, despite their treatment with water, but are notable for their bulk densities of more than 0.6 g/ml, their spherical shape and their smooth surface. The product thus obtained is particularly suitable for coating with a gastric-juice-resistant coating. The resultant particles with their smooth surface, which are prepared according to the invention, are suitable for direct coating with a gastric-juice-resistant film.

The filming of pancreatin products, e.g. tablets or pellets, is difficult. In the literature, processes are described which involve several working steps and are time-consuming. The particular problem of filming is attributed to the lability of the enzymes, the porous structure of the surface and the stability of the film coatings.

In EP 0021129, a process is described in which pellets produced by extrusion are treated with a solution of polyvinylpyrrolidone, a synthetic binding agent, and optionally polyethylene glycol 6000 to produce smoothed pellets. Only these modified pellets can be coated with a solution of the film-forming material in an organic solvent mixture. The use of organic solvents is however limited for ecological reasons.

In EP 0184754, a process is described in which pancreatin products are given one or several covering layers, and are only then coated with gastric-juice-resistant layers. Coating is time-consuming. The dragees obtained have a high proportion by weight of filler, so that the enzyme content in the finished dragee is relatively low. In EP 0166315, micro-tablets are prepared from pancreatin powder in a technologically complicated process. These micro-tablets may have a gastric-juice-resistant film covering.

In the process according to the invention, the gastric-juice-resistant filming of the pancreatin particles may be carried out without special pre-treatment, with, in particular, aqueous solutions of film-forming materials. The proportion by weight of the covering material in the finished product should be kept as low as possible. Because of the spherical shape and resultant smaller surface, and also because of the especially smooth surface, resistance to gastric juices may be attained with a coating of only circa 15% the particle weight, while previously higher amounts were necessary. Upon filling into capsules, this small coating and the high bulk density provide a high enzyme dosage per capsule. Thus the process of the invention requires a small number of production steps, especially drying steps, yet provides a higher specific activity (units per mg) than with comparable products.

In a further aspect the invention accordingly provides spherical pancreatin particles having a smooth surface and having a diameter of 0.3 to 4 mm, free from added binder. The pancreatin particle is thus free from binders, e.g. polyvinylpyrrolidone or polyethylene glycol. Preferably the particle is free or substantially free from non-natural excipients such as lubricants. The pancreatin will of course contain natural products associated with pancreatin preparation e.g. natural enzymes, natural mineral salts and fat.

In another aspect the invention provides a pharmaceutical composition produced from pancreatin particles according to the invention e.g. gastric juice resistant pancreatin particles coated with a gastric juice resistant film the weight of which is less than 50 percent of the uncoated particle.

Filming may be carried out for example as follows:

The pellets produced according to the invention, with a smooth surface and a grain size of 0.3–4 mm (preferably 0.8–2.5 mm in diameter), are coated with an aqueous or organic solution of film-forming materials in commercial high-temperature filming or fluidized bed devices. The gastric-juice-resistant film-forming materials may be conventional excipients such as cellulose acetate phthalate, hydroxypropyl methylcellulose phthalate, polyvinylacetate phthalate and copolymers based on methacrylic acid and esters thereof (e.g. the brand Eudragit). In order to attain the necessary film elasticity, softeners may be added, such as a citric acid ester (e.g. the brand Citroflex), polyethylene glycol, dibutyl phthalate, 1,2-propylene glycol, in quantities of 5–30%, based on the film-forming material. To prevent undesirable agglomeration during the filming process, known separating agents can be added to the film suspension, such as talc, magnesium stearate, calcium triphosphate and the like. The amount of gastric-juice-resistant film coating may be 5–50%, preferably 10–30% e.g. 10–20% of the pancreatin weight, i.e. the weight of the uncoated particles.

To improve stability in storage, it may be desired to prevent direct contact between pancreatin and gastric-juice-resistant coating. With this in mind, the pancreatin particles may have a layer between the coating and pancreatin consisting e.g. of cellulose derivatives, such as hydroxypropyl cellulose, hydroxypropyl methylcellulose or methylcellulose.

The gastric juice resistance of the gastric-juice-resistant pancreatin particles according to the invention may correspond to the requirements of the European Pharmacopeia. The enzyme activity remains complete upon incubation in hydrochloric acid pH 1 at 37° C. for 2 hours. Upon reaching the physiological pH value of the duodenum, the enzymes are released rapidly and completely from the particles. The gastric-juice-resistant film cited particles produced in the examples meet these requirements.

The following Examples illustrate the invention without limiting its scope.

Furthers details on characteristics of excipients as described herein may be obtained from manufacturer's brochures and standard reviews, e.g. H.P.Fiedler, Lexikon der Hilfstoffe fuer Pharmazie, Kosmetik, und angrenzende Gebiete, Aulendorf, 3rd Edition 1989 and Handbook of Pharmaceutical Excipients, American Pharmaceutical Association and the Pharmaceutical Society of Great Britain, 1986.

EXAMPLE 1

Preparation of particles with a low bulk density and soft surface 4000 l of acetone are added to 1000 kg of pancreas pulp and stirred for about one hour in a extraction vessel of 8000 l content. The mixture is then centrifuged and the residue twice undergoes treatment in the same way, each time with 3000 l of acetone. After centrifuging again, the acetone-moist solid panceatin pulp is dispersed in ten equal portions for about 17 minutes in the tray of a vacuum cutter (supplied by e.g. Kraemer & Grebe, 3562 Wallau/Lahn, Federal Republic of Germany) of ca. 120 l content. The rotational speed of the tray is 18 rpm, and the rotational speed of the rotating hives is 2965 rpm. The mass is transformed into spherical particles of ca. 0.3 to 1.0 mm diameter. The vacuum is then removed and the particles treated for a further 5 minutes in the cutter. Afterwards the product is dried in a double cone vacuum drier.

The resultant dry pancreatin particles are obtained in a yield of 206 kg and has the following analysis:

| content of | |
|---|---|
| lipase: | 56.9 FIP Units/mg |
| amylase: | 45.4 FIP Units/mg |
| activated protease: | 3.39 FIP Units/mg |
| fat: | 0.7% |
| drying loss: | 1.9% |
| bulk density: | 0.41 g/ml |
| grain size: | 80% between 0.35 and 0.85 mm |

The material corresponds to the requirements of the Eur. Pharm. and can be used directly for galenic processing, especially for pressing into tablets.

EXAMPLE 2

Preparation of particles with a higher bulk density and medium-hard surface 1000 kg of pancreas pulp is subjected to acetone extraction three times, as described in Example 1. The acetone-moist pancreas pulp obtained after the last separation step is dispersed in ten equal portions into the tray of the above described vacuum cutter, mixed with 1.0 l of water per portion, and shaped into spherical particles under vacuum for ca. 12 minutes. After further treatment in the cutter—ca. 18 minutes without vacuum—the product is dried in a double cone vacuum drier.

The resultant dry pancreatin product is obtained in a yield of 207 kg, and has the following analysis:

| content of | |
|---|---|
| lipase: | 55.3 FIP Units/mg |
| amylase: | 40.9 FIP Units/mg |
| activated protease: | 3.39 FIP Units/mg |
| fat: | 1.4% |
| drying loss: | 2.1% |
| bulk density: | 0.51 g/ml |
| grain size: | 80% between 0.30 and 0.85 mm |

The product corresponds to the Eur. Pharm. and can be used directly for galenic processing, especially for filling capsules and also for pressing into tablets.

EXAMPLE 3

Preparation of particles from pancreatin concentrate

The pancreatin concentrate pulp, which is moist with solvent and has been prepared by the conventional processes, is introduced in ca. 40 kg portions into the vacuum cutter described in Example 1. 0.5 l of water is added per liter volume of the tray, and shaping into spherical particles is undertaken over 15 minutes under vacuum in the cutter. For a further 5 minutes, the product is aerated without vacuum in the cutter, and is subsequently dried in a double cone vacuum drier.

The resultant pancreatin dry particle concentrate corresponds in bulk density, grain size, fat and drying loss to the products listed in Examples 1 and 2, but the enzyme activity is higher, as expected with a concentrate. The product may be used directly, without further treatment, for galenic processing.

EXAMPLE 4

Preparation of particles with a high bulk density and hard, smooth surface 1000 kg of pancreas pulp is subjected to acetone extraction three times, as described in Examples 1 and 2. The acetone-moist pancreas pulp obtained after the last separation step is introduced in ten equal portions into the described vacuum cutter, mixed with 2.5 l of water per portion, and shaped into spherical particles under vacuum for ca. 12 minutes. After further treatment in the cutter—ca. 18 minutes without vacuum—the particles are dried in a double cone vacuum drier.

The resultant dry pancreatin product is obtained in a yield of 210 kg, and has the following analysis:

content of

| | |
|---|---|
| lipase: | 49.4 FIP Units/mg |
| amylase: | 44.8 FIP Units/mg |
| activated protease: | 3.14 FIP Units/mg |
| fat: | 1.5% |
| drying loss: | 2.9% |
| bulk density: | 0.71 g/ml |
| grain size: | 80% between 0.5 and 1.5 mm |

The product corresponds to the requirements of the Eur. Pharm. and can be used without further processing for filling into capsules. Because of their smooth surface, the particles are especially suitable for covering with gastric-juice-resistant coatings.

EXAMPLE 5

Preparation of particles with a high bulk density and hard, smooth surface, from particles having low bulk density Pancreatin particles, produced in analogous manner to the process described in Examples 1 and 2, are sieved and the fine portions of less than 1.2 mm are separated. 20 kg of this coarse granulate thus obtained are introduced to the described vacuum cutter, and sprayed with 3.5 l of water using an atomizer nozzle at a low rotational speed of vessel and hives. After mixing for 15 minutes, the particles which are moist with water is introduced into a double cone vacuum drier, in which 60 l of acetone is present, and dried. The acetone prevents a drastic increase in bacterial count and considerable reduction in enzyme activity. The reduction in lipase activity is max. 10%, and in amylase activity it is max. 5%.

The resultant, coarse-grained particles have the following analysis, the analysis of the starting particles being placed in parentheses for comparison:

content of

| | |
|---|---|
| lipase: | 45.8 (50.7) FIP Units/mg |
| amylase: | 39.4 (41.7) FIP Units/mg |
| activated protease: | 3.47 (3.49) FIP Units/mg |
| fat: | 0.4 (0.7)% |
| drying loss: | 2.3 (2.4)% |
| bulk density: | 0.62 (0.42) g/ml |
| grain size: | 90% between 1.2 and 2.0 mm |

The product corresponds to the Eur. Pharm. and can be used directly for galenic processing—preferably for filling into capsules. Because of its physical properties, it is especially suitable for covering with gastric-juice-resistant coatings, as with the product described in Example 4.

EXAMPLE 6

Preparation of particles from dried pancreatin powder and/or dried powdery enzyme concentrate 15 kg of pancreatin powder and 5 kg of powdery pancreatin enzyme concentrate are dispersed in the tray of the cutter described in Example 1, and mixed with 20 l of acetone and 1 l of water. The acetone-moist pulp is shaped into spherical particles in the vacuum cutter, as described in Example 2, and dried in a double cone vacuum drier.

The dry product which is produced without loss of yield is obtained with the following analysis:

content of

| | |
|---|---|
| lipase: | 49.1 FIP Units/mg |
| amylase: | 40.5 FIP Units/mg |
| activated protease: | 2.20 FIP Units/mg |
| fat: | 0.5% |
| drying loss: | 3.3% |
| bulk density: | 0.47 g/ml |
| grain size: | 80% between 560 and 1150 µm |

The enzyme losses are comparable with the losses in the process described in Example 5. The product corresponds to the Eur. Pharm. and can be used directly for galenic processing, especially for pressing into tablets.

EXAMPLE 7

Preparation of gastric-juice-resistant pellets 1. 500 g of pancreatin particles are covered with a gastric-juice-resistant film in a fluidised bed appliance (Aeromatic, size 1) using a solution consisting of:

| | |
|---|---|
| Eudragit L 30 D | 278.0 g |
| Triethyl citrate (Citroflex 2) | 16.7 g |
| water | 261.3 g |

The gastric-juice-resistant pancreatin particles thus obtained have a coating of 20% by weight of pancreatin (17% by weight of particles).

2. 8,000 g of pancreatin particles are covered with a gastric-juice-resistant film in a fluidized bed plant having a modified film coating unit (GLATT WSG 15) using a solution of:

| | |
|---|---|
| hydroxypropylmethyl cellulose phthalate (HP 55) | 1,230 g |
| dibutyl phthalate | 370 g |
| methanol | 7,900 g |
| methylene chloride | 5,500 g |

3. 8,000 g of pancreatin particles are firstly pre-coated in a fluidized bed plant having a spray-granulating unit (GLATT WSG 15) using a solution of:

| | |
|---|---|
| Methylcellulose (brand Methocel E 15) | 160 g |
| talc | 40 g |
| water | 3,000 g | and then covered with a gastric-juice-resistant film, using a solution of:

| | |
|---|---|
| Polymethacrylate (brand Eudragit L 100-55) | 1,600 g |
| sodium hydroxide 1 N | 541 g |
| polyethylene glycol 6000 | 320 g |
| water | 8,200 g |
| talc | 350 g. |

We claim:

1. A process for producing pancreatin particles comprising the steps of:
   (i) providing a pancreatin mass moist with water and another suitable solvent under at least initially evacuated conditions and rotating the mass around a first axis; and (ii) providing knives rotatable around a second axis which is disposed at a selected angle relative to the first axis, and simultaneously rotating the mass and knives about their respective axes at different speeds to cut and reduce the size of the mass, creating spherical particles, while some of the solvent is removed.

2. A process according to claim 1 wherein the pancreatin mass is moist with acetone containing water.

3. A process according to claim 1 wherein the pancreatin mass is converted directly to a galenical form having a particle size of 0.3 to 4 mm.

4. A process according to claim 3 wherein the particles are subsequently dried.

5. A process according to claim 3 wherein the particles are coated with a gastric juice resistant film.

6. A spherical pancreatin particle having a smooth surface and having a diameter of from 0.3 to 4 mm produced by a process according to claim 1, 2, 3, 4 of 5.

7. A pharmaceutical composition comprising pancreatin particles made according to the process of claim 6.

8. A pharmaceutical composition comprising gastric juice resistant pancreatin particles as claimed in claim 6 coated with a gastric Juice resistant film, the weight of which is less than 50 percent of the uncoated particles.

9. A pharmaceutical composition according to claim 8 wherein the spherical particles are free from added binder.

* * * * *